United States Patent
Saltzman

(10) Patent No.: US 12,090,179 B2
(45) Date of Patent: *Sep. 17, 2024

(54) METHODS OF SYNERGISTIC TREATMENT OF CANCER

(71) Applicant: Salspera, LLC, Oakdale, MN (US)

(72) Inventor: Daniel A. Saltzman, Mendota Heights, MN (US)

(73) Assignee: Salspera, LLC, Oakdale, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/159,934

(22) Filed: Jan. 26, 2023

(65) Prior Publication Data

US 2024/0091275 A1    Mar. 21, 2024

Related U.S. Application Data

(62) Division of application No. 16/467,338, filed as application No. PCT/US2017/064813 on Dec. 6, 2017, now Pat. No. 11,576,936.

(60) Provisional application No. 62/430,962, filed on Dec. 7, 2016.

(51) Int. Cl.
| | |
|---|---|
| *A61K 35/74* | (2015.01) |
| *A61K 31/513* | (2006.01) |
| *A61K 31/555* | (2006.01) |
| *A61K 31/675* | (2006.01) |
| *A61K 31/7068* | (2006.01) |
| *A61K 33/243* | (2019.01) |

(52) U.S. Cl.
CPC ............ *A61K 35/74* (2013.01); *A61K 31/513* (2013.01); *A61K 31/555* (2013.01); *A61K 31/675* (2013.01); *A61K 31/7068* (2013.01); *A61K 33/243* (2019.01)

(58) Field of Classification Search
CPC .... A61K 35/74; A61K 31/513; A61K 31/555; A61K 31/675; A61K 31/7068; A61K 33/243
See application file for complete search history.

(56) References Cited

U.S. PATENT DOCUMENTS

| | | |
|---|---|---|
| 6,685,935 B1 | 2/2004 | Pawelek et al. |
| 7,588,767 B2 | 9/2009 | Szalay et al. |
| 8,066,987 B2 | 11/2011 | Moore et al. |
| 8,221,739 B2 | 7/2012 | Leonard et al. |
| 8,647,618 B2 | 2/2014 | Leonard et al. |
| 2005/0244375 A1 | 11/2005 | Leonard et al. |
| 2006/0105423 A1 | 5/2006 | Rapp et al. |
| 2007/0128301 A1 | 6/2007 | Saltzman et al. |
| 2007/0243310 A1 | 10/2007 | Leonard et al. |
| 2008/0107758 A1 | 5/2008 | Crutchfield |
| 2010/0098665 A1 | 4/2010 | Leonard et al. |
| 2013/0045525 A1 | 2/2013 | Leonard et al. |
| 2013/0295054 A1 | 11/2013 | Huang et al. |

FOREIGN PATENT DOCUMENTS

| | | |
|---|---|---|
| EP | 833660 B1 | 12/2006 |
| EP | 2028270 A2 | 2/2009 |
| JP | 7249279 B2 | 3/2023 |
| WO | 0032211 A1 | 6/2000 |
| WO | 0124637 A1 | 4/2001 |
| WO | 0226819 A2 | 4/2002 |
| WO | 03063593 A1 | 8/2003 |
| WO | 03072789 A2 | 9/2003 |
| WO | 2005116233 A1 | 12/2005 |
| WO | 2005116233 A2 | 12/2005 |
| WO | 2007025333 A1 | 3/2007 |
| WO | 2007039192 A2 | 4/2007 |
| WO | 2016145974 A1 | 9/2016 |
| WO | 2018106754 A1 | 6/2018 |

OTHER PUBLICATIONS

Abdulamir et al., "The tumoricidal activity of *Salmonella* and its role in treating cancers", Cancer Therapy, vol. 3, No. 8, Feb. 14, 2013, pp. 10-23.
European Patent Application No. 17877671.2, Extended European Search Report mailed May 12, 2020, 8 pages.
Forbes et al., "White paper on microbial anti-cancer therapy and prevention," Journal for ImmunoTherapy of Cancer, vol. 6, No. 1, 2018, 24 pages.
Wasiluk et al. "QS310. Attenuated *Salmonella Typhimurium* Expressing Human Interleukin-2 (IL-2) Invades Human Pancreatic Cancer Cells", Journal of Surgical Research, Feb. 2008, pp. 1-8, vol. 144 Issue 2.
Noone et al., "SEER Cancer Statistics Review, 1975-2015," National Cancer Institute, 2018, 102 pages.
Curtiss III et al., "*Salmonella typhimurium* Deletion Mutants Lacking Adenylate Cyclase and Cyclic AMP Receptor Protein Are Avirulent and Immunogenic," Infection and Immunity, vol. 55, No. 12, Dec. 1987, pp. 3035-3043.

(Continued)

*Primary Examiner* — Kade Ariani

(74) *Attorney, Agent, or Firm* — Fredrikson & Byron, P.A.

(57) ABSTRACT

A method of treating cancer includes administering a dose of a chemotherapy agent in combination with a dose of a composition consisting essentially of attenuated *Salmonella typhimurium*. The dose of the chemotherapy agent is lower than a maximum effective dose of the chemotherapy agent. The combination provides a synergistic reduction in tumor burden when compared to the reduction in tumor burden provided by administration of an equivalent dose of the chemotherapy agent without the composition consisting essentially of attenuated *Salmonella typhimurium*.

16 Claims, 6 Drawing Sheets

Specification includes a Sequence Listing.

(56) References Cited

OTHER PUBLICATIONS

Gulig et al., "Plasmid-Associated Virulence of *Salmonella typhimurium*," Infection and Immunity, vol. 55, No. 12, Dec. 1987, pp. 2891-2901.
Galan et al., "Cloning and characterization of the asd gene of *Salmonella typhimurium*: use in stable maintenance of recombinant plasmids in *Salmonella* vaccine strains," Gene, vol. 94, 1990, pp. 29-35.
Ustun et al., "Investigation of technological properties of *Nigella sativa* (Black Cumin) seed oil," JAOCS, vol. 67, No. 12, Dec. 1990, pp. 958-960.
Schodel et al., "Hybrid hepatitis B virus core-pre-S proteins synthesized in avirulent *Salmonella typhimurium* and *Salmonella typhi* for oral vaccination", Infect Immun., vol. 62, No. 5, May 1994, pp. 1669-1676.
Saltzman et al. "Attenuated *Salmonella typhimurium* Containing Interleukin-2 Decreases MC-38 Hepatic Metastases: A Novel Antitumor Agent," Cancer Biotherapy and Radiopharmaceuticals, vol. 11, No. 2, 1996, pp. 145-153.
Eckenberg et al., "Analysis of Human IL-2/IL-2 Receptor B chain interactions: Monoclonal Antibody H2-8 and new IL-2 Mutants define the critical role of a Helix-A of IL-2," Cytokine, vol. 9, No. 7, 1997, pp. 488-498.
Saltzman et al., "Antitumor Mechanisms of Attenuated *Salmonella typhimurium* Containing the Gene for Human Interleukin-2: A Novel Antitumor Agent?" Journal of Pediatric Surgery, vol. 32, No. 2, Feb. 1997, pp. 301-306.
Saltzman et al., "Patterns of Hepatic and Splenic Colonization for the Attenuated *Salmonella typhimurium* Containing the Gene for Human Interleukin-2: A Novel Anti-Tumor Agent," Cancer Biotherapy & Radiopharmaceuticals, vol. 12, No. 1, Feb. 1997, pp. 37-45.
Owen et al., "The antioxidant/anticancer potential of phenolic compounds isolated from olive oil," European Journal of Cancer, vol. 36, 2000, pp. 1235-1247.
Therasse et al., "New Guidelines to Evaluate the Response to Treatment in Solid Tumors," Journal of the National Cancer Institute, vol. 92, No. 3, Feb. 2, 2000, pp. 205-216.
Feltis et al., "Cyclooxygenase 2 inhibition augments the hepatic antitumor effect of oral *Salmonella typhimurium* in a model of mouse metastatic colon cancer," Diseases of the Colon and Rectum, vol. 45, No. 8, Aug. 2002, pp. 1023-1028.
Feltis et al., "Liver and Circulating NK1.1+CD3-Cells Are Increased in Infection with Attenuated *Salmonella typhimurium* and Are Associated with Reduced Tumor in Murine Liver Cancer," Journal of Surgical Research, vol. 107, No. 1, Sep. 2002, pp. 101-107.
Toso et al., "Phase I Study of the Intravenous Administration of Attenuated *Salmonella typhimurium* to Patients with Metastatic Melanoma," Journal of Clinical Oncology, vol. 20, No. 1, Jan. 2002, pp. 142-152.
Wada et al., "Antioxidant Activity and Phenolic Content of Oregon Caneberries," Journal of Agricultural and Food Chemistry, vol. 50, No. 12, Jun. 5, 2002, pp. 3495-3500.
Atta, "Some characteristics of nigella (*Nigella sativa* L.) seed cultivated in Egypt and its lipid profile," Food Chemistry, vol. 83, 2003, p. 63.
Nelson, "Antioxidant oil augments cytotoxic immune response to attenuated *Salmonella typhimurium*," Department of Surgery, University, XP-002460183, Apr. 30, 2003.
Parker et al., "Fatty Acid Composition and Oxidative Stability of Cold-pressed Edible Seed Oils," Journal of Food Science, vol. 68, No. 4, 2003, pp. 1240-1243.
Soto et al., "Attenuated *Salmonella typhimurium* prevents the Establishment of Unresectable Hepatic Metastases and Improves Survival in a Murine Model," Journal of Pediatric Surgery, vol. 38, No. 7, 2003, pp. 1075-1079.
Trotti et al., "CTCAE v3.0: Development of a Comprehensive Grading System for the Adverse Effects of Cancer Treatment," Seminars in Radiation Oncology, vol. 13, No. 3, Jul. 2003, pp. 176-181.

Parry et al., "Fatty acid content and antioxidant properties of cold-pressed black raspberry seed oil and meal," Journal of Food Science, vol. 69, No. 3, 2004, pp. 189-193.
Soto et al., "Attenuated *Salmonella typhimurium*-Induced Immunity to Hepatic Colorectal Metastases," Surgery, University of Minnesota, SSO 57th Annual Cancer Symposium, Abstract p. 79, 2004, p. S107.
Soto et al., "Preferential Proliferation of Attenuated *Salmonella typhimurium* Within Neuroblastoma," Journal of Pediatric Surgery, vol. 39, No. 6, 2004, pp. 937-940.
Barnett et al., "*Salmonella typhimurium* Invades and Decreases Tumor Burden in Neuroblastoma," Journal of Pediatric Surgery, vol. 40, No. 6, 2005, pp. 993-998.
Saltzman, "Cancer immunotherapy based on the killing of *Salmonella typhimurium*-infected tumour cells," Expert Opinion on Biological Therapy, vol. 5, No. 4, 2005, pp. 443-449.
Verma et al., "Gene Therapy: Twenty First Century Medicine," Annual Review of Biochemistry, vol. 74, 2005, pp. 711-738.
Kimchi-Sarfaty et al., "A Silent Polymorphism in the MDR1 Gene Changes Substrate Specificity" Science, vol. 315, Jan. 2007, pp. 525-528.
Sorenson et al., "Attenuated *Salmonella typhimurium* with IL-2 Gene Reduces Pulmonary Metastases in Murine Osteosarcoma," Clinical Orthopaedics and Related Research, vol. 466, No. 6, Jun. 1, 2008, pp. 1285-1291.
Sorenson et al., "Attenuated *Salmonella typhimurium* with interleukin 2 gene prevents the establishment of pulmonary metastases in a model of osteosarcoma," Journal of Pediatric Surgery, vol. 43, 2008, pp. 1153-1158.
Wasiluk et al., "QS310. Attenuated *Salmonella Typhimurium* Expressing Human Interleukin-2 (IL-2) Invades Human Pancreatic Cancer Cells", Oncology IX: Apoptosis, Immunology, and Angiogenesis, vol. 144, Issue 2, p. 390, Feb. 2008, pp. 1-5.
Forbes, "Engineering the perfect (bacterial) cancer therapy," Nature Reviews Cancer, Advance Online Publication, 2010, 10 pages.
Sorenson et al., "Safety and immunogenicity of *Salmonella typhimurium* expressing C-terminal truncated human IL-2 in a murine model," Biologics: Targets & Therapy, vol. 4, 2010, pp. 61-73.
Conroy et al., "Folfirinox versus Gemcitabine for Metastatic Pancreatic Cancer," The New England Journal of Medicine, vol. 364, No. 19, May 12, 2011, pp. 1817-1825.
Zhang et al., "Determination of the Optimal Route of Administration of *Salmonella typhimurium* A1-R to Target Breast Cancer in Nude Mice," Anticancer Research, vol. 32, pp. 2501-2508, 2012.
Abdulamir et al., "The tumoricidal activity of *Salmonella* and its role in treating cancers", Cancer Therapy, vol. 8, No. 8, Feb. 14, 2013, pp. 10-23.
Lesterhuis et al., "Synergistic Effect of CTLA-4 Blockade and Cancer Chemotherapy in the Induction of Anti-Tumor Immunity," PLoS One, vol. 8, No. 4, Apr. 2013, pp. 1-8.
Saltzman, "Project Stealth: Daniel Saltzman at TEDxCarletonCollege," TEDx Talks, published Nov. 30, 2013, Retrieved online from <https://www.youtube.com/watch?v=2gUBvjdlymE> on May 17, 2019, 2 pages.
Drees et al., "Soluble production of a biologically active single-chain antibody against murine PD-L1 in *Escherichia coli*," Protein Expression and Purification, vol. 94, Feb. 2014, pp. 60-66.
Hiroshima et al. "Efficacy of Tumor-Targeting Salmonella Typhimurium A1-R in Combination with Anti-Angiogenesis Therapy on a Pancreatic Cancer Patient-derived orthotopic xenograft (PDOX) and cellline mouse models", Oncotarget vol. 5 No. 23, Oct. 28, 2014, pp. 12346-12357.
Drees et al., "Attenuated *Salmonella enterica* Tyhimurium Reduces Tumor Burden in an Autochthonous Breast Cancer Model," Anticancer Research: International Journal of Cancer Research and Treatment, vol. 35, 2015, pp. 843-850.
Drees et al., "Vasculature Disruption Enhances Bacterial Targeting of Autochthonous Tumors," Journal of Cancer, vol. 6, No. 9, 2015, pp. 843-848.
Fritz et al., "A phase I clinical study to evaluate safety of orally administered, genetically engineered *Salmonella enterica* serovar Typhimurium for canine osteosarcoma," Veterinary Medicine and Science, vol. 2, No. 3, Jun. 6, 2016, pp. 179-190.

(56) References Cited

OTHER PUBLICATIONS

Mercado-Lubo et al., "A *Salmonella* nanoparticle mimic overcomes multidrug resistance in tumours," Nature Communications, vol. 7, No. 12225, Jul. 25, 2016, 13 pages.

Murakami et al., "Tumor-targeting *Salmonella typhimurium* A1-R in combination with doxorubicin eradicate soft tissue sarcoma in a patient-derived orthotopic xenograft (PDOX) model," Oncotarget, vol. 7, No. 11, Mar. 15, 2016, pp. 12783-12790.

Carrega et al., "Natural Killers Are Made Not Born: How to Exploit NK Cells in Lung Malignancies," Frontiers in Immunology, vol. 8, Article 277, Mar. 2017, 7 pages.

International Patent Application No. PCT/US2017/064813, International Search Report & Written Opinion mailed May 18, 2018, 16 pages.

Neoptolemos et al., "Comparison of adjuvant gemcitabine and capecitabine with gemcitabine monotherapy in patients with resected pancreatic cancer (ESPAC-4): a multicentre, open-label, randomised, phase 3 trial", Lancet vol. 389, Jan. 25, 2017, pp. 1011-1024.

Conroy et al., "Folfirinox or Gemcitabine as Adjuvant Therapy for Pancreatic Cancer", The New England Journal of Medicine, vol. 379 No. 25, Dec. 20, 2018, pp. 2395-2406.

Flickinger Jr. et al., "Listeria monocytogenes as a Vector for Cancer Immunotherapy: Current Understanding and Progress," Vaccines, vol. 6, No. 3, 2018, 19 pages.

Sorenson et al., "Attenuated *Salmonella typhimurium* with IL-2 Gene Reduces Pulmonary Metastases in Murine Osteosarcoma", Clinical Orthopedics and Related Research, vol. 466, No. 6, Jun. 2008, pp. 1285-1291.

Forbes et al., "White paper on microbial anti-cancer therapy and prevention", Journal for Immunotherapy of Cancer, Biomed Central Ltd, vol. 6 No. 1, Aug. 6, 2018, pp. 1-24.

Batist et al., "Orally Administered Multiple Dose Saltikva (*Salmonella*-IL2) in Conjunction with Folfirinox in a Patient with Stage IV Pancreatic Cancer: A Case Report", Clinical Oncology: Case Reports vol. 3 No. 3, Jun. 2, 2020, pp. 1-4.

Aston et al. "A systemic investigation of the maximum tolerated dose of cytotoxic chemotherapy with and without supportive care in mice" BMC Cancer, vol. 17, No. 684, pp. 1-10.

Saltzman et al., "Low dose chemotherapy combined with attenuated *Salmonella* decreases tumor burden and is less toxic than high dose chemotherapy in an autochthonous murine model of breast cancer," Surgery, vol. 163, No. 3, 2018, pp. 509-514.

Yang et al., "*Salmonella* Overcomes Drug Resistance in Tumor through P-glycoprotein Downregulation," International Journal of Medical Sciences, vol. 15, 2018, pp. 574-579.

Mi et al., "*Salmonella*-Mediated Cancer Therapy: An Innovative Therapeutic Strategy," Journal of Cancer, vol. 10, No. 20, Aug. 20, 2019, pp. 4765-4776.

Batist et al., "Orally Administered Multiple Dose Saltikva (*Salmonella*-IL2) in Conjunction with Folfirinox in a Patient with Stage IV Pancreatic Cancer: A Case Report," Clinical Oncology: Case Reports, vol. 3, Issue 3, Jun. 2, 2020, 4 pages.

Gniadek et al., "A Phase I, Dose Escalation, Single Dose Trial of Oral Attenuated *Salmonella typhimurium* Containing Human IL-2 in Patients With Metastatic Gastrointestinal Cancers," Journal of Immunotherapy, vol. 43, No. 7, Sep. 2020, pp. 217-221.

International Patent Application No. PCT/US2020/067067, International Search Report & Written Opinion mailed May 26, 2021, 14 pages.

METHODS OF SYNERGISTIC TREATMENT OF CANCER

RELATED APPLICATIONS

This application is a divisional of U.S. application Ser. No. 16/467,338, filed Jun. 6, 2019, and entitled "Methods of Synergistic Treatment of Cancer," which was filed under 35 U.S.C. § 371 and claims priority to International PCT Application No. PCT/US2017/064813, filed on Dec. 6, 2017 and entitled "Methods of Synergistic Treatment of Cancer," which claims benefit to U.S. Provisional Application No. 62/430,962, filed Dec. 7, 2016, the entire contents of all which are incorporated herein by reference.

SEQUENCE LISTING XML

The instant application contains a sequence listing, which has been submitted in XML file format by electronic submission and is hereby incorporated by reference in its entirety. The XML file, created on Jan. 18, 2023, is named 84977-3-3-1_Sequence Listing.xml and is 2,981 bytes in size.

TECHNICAL FIELD

This disclosure relates to methods of treating cancer, and more particularly, to methods of treating cancer with attenuated *Salmonella typhimurium*.

BACKGROUND

Despite continuing efforts of fighting cancer, nearly 600,000 cancer-related deaths still occur in the United States each year, and over 8 million cancer-related deaths occur worldwide. Thus, according to the World Health Organization, cancer continues to be a leading cause of morbidity and mortality worldwide. In addition, it is expected that annual cancer cases will rise from 14 million in 2012 to 22 million within the next two decades. The mainstay of cancer treatment is chemotherapy with the aim of curing or controlling this disease with the maximum tolerated dose (MTD) or the highest dose of a drug with tolerable side effects. Strategies employed to decrease the side effects include, for example, varying the combination of anti-neoplastic agents, metronomic dosing, and delivery of the chemotherapeutic agent directly to the affected organ. In the last several years, advancements have been made with immunotherapy for cancer treatment and many immunologic agents have demonstrated promise in this field. However, significant toxicities and tumor resistance limit this treatment strategy.

SUMMARY

In general, this disclosure relates to methods of treating cancer with *Salmonella typhimurium*. A dose of a chemotherapy agent is administered in combination with a dose of attenuated *Salmonella typhimurium*. The dose of the chemotherapy agent is lower than a maximum effective dose of the chemotherapy agent. The attenuated *Salmonella typhimurium* can include a truncated interleukin-2 gene. The combination provides a synergistic effect that provides a greater reduction in tumor burden than the administration of an equivalent dose of the chemotherapy agent alone. As a result, a lower and less toxic dose of the chemotherapy agent can be used, which provides effective treatment while minimizing side effects caused by the toxicity of the chemotherapy agent.

In one embodiment, a method of treating cancer includes administering a combination of a dose of a chemotherapy agent and a dose of a composition consisting essentially of attenuated *Salmonella typhimurium*. The dose of the chemotherapy agent is lower than a maximum effective dose of the chemotherapy agent. The combination provides a synergistic reduction in tumor burden when compared to the reduction in tumor burden provided by administration of an equivalent dose of the chemotherapy agent without the composition consisting essentially of attenuated *Salmonella typhimurium*. The toxicity of the combination is lower than the toxicity of the maximum effective dose of the chemotherapy agent.

In another embodiment, a method of treating cancer includes administering a combination of a dose of a chemotherapy agent and a dose of attenuated *Salmonella typhimurium* containing a plasmid carrying a coding sequence encoding a truncated human interleukin-2, wherein the truncated human interleukin-2 consists of the amino acid sequence shown in SEQ ID NO: 2. The dose of the chemotherapy agent is lower than a maximum effective dose of the chemotherapy agent. The combination provides a synergistic reduction in tumor burden when compared to the reduction in tumor burden provided by administration of an equivalent dose of the chemotherapy agent without the attenuated *Salmonella typhimurium* containing the plasmid carrying the coding sequence encoding the truncated human interleukin-2. The toxicity of the combination is lower than the toxicity of the maximum effective dose of the chemotherapy agent.

In another embodiment, an anti-tumor agent for use in a method of treating cancer includes a combination of a dose of a chemotherapy agent and a dose of a composition consisting essentially of attenuated *Salmonella typhimurium*. The method includes administering the combination of the dose of the chemotherapy agent and the dose of the composition consisting essentially of attenuated *Salmonella typhimurium*. The dose of the chemotherapy agent is lower than a maximum effective dose of the chemotherapy agent. The combination provides a synergistic reduction in tumor burden when compared to the reduction in tumor burden provided by administration of an equivalent dose of the chemotherapy agent without the composition consisting essentially of attenuated *Salmonella typhimurium*. The toxicity of the combination is lower than the toxicity of the maximum effective dose of the chemotherapy agent.

In another embodiment, an anti-tumor agent for use in a method of treating cancer includes a combination of a dose of a chemotherapy agent and a dose of attenuated *Salmonella typhimurium* containing a plasmid carrying a coding sequence encoding a truncated human interleukin-2, wherein the truncated human interleukin-2 consists of the amino acid sequence shown in SEQ ID NO: 2. The method includes administering the dose of the chemotherapy agent in combination with the dose of attenuated *Salmonella typhimurium* containing the plasmid carrying the coding sequence encoding the truncated human interleukin-2. The dose of the chemotherapy agent is lower than a maximum effective dose of the chemotherapy agent. The combination provides a synergistic reduction in tumor burden when compared to the reduction in tumor burden provided by administration of an equivalent dose of the chemotherapy agent without the attenuated *Salmonella typhimurium* containing the plasmid carrying the coding sequence encoding the truncated human interleukin-2. The toxicity of the combination is lower than the toxicity of the maximum effective dose of the chemotherapy agent.

DETAILED DESCRIPTION

Figure 1A:
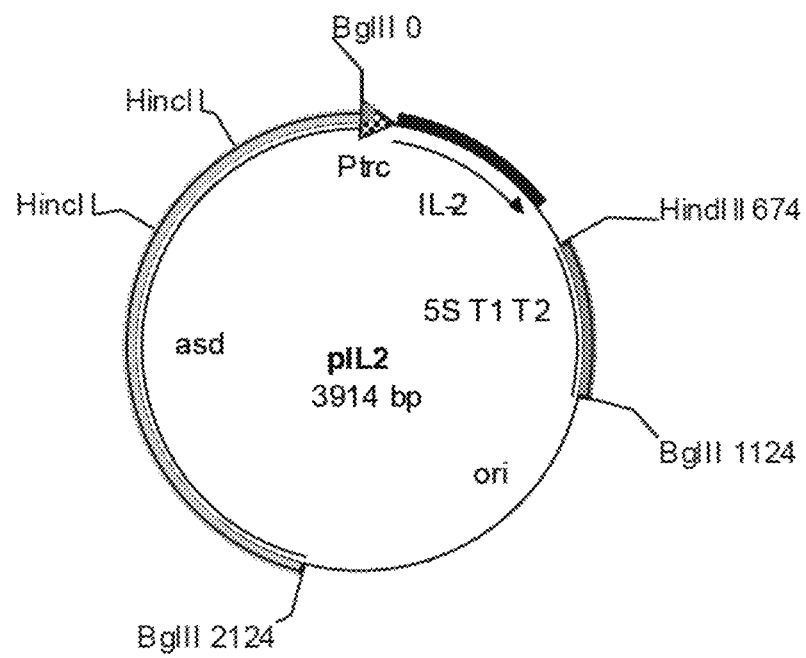
FIG. 1A shows the pIL2 plasmid containing the coding sequence encoding the human interleukin-2 protein, used to construct SalpIL2, attenuated *S. typhimurium* with the IL-2 gene.
Figure 1B:
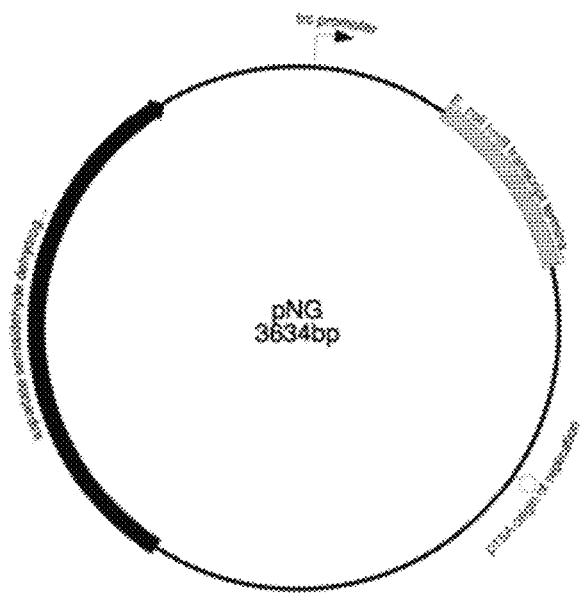
FIG. 1B shows the pNG.1 plasmid without the coding sequence encoding the human interleukin-2 protein, used to construct SalpNG.1, attenuated *S. typhimurium* without the IL-2 gene.

The following detailed description is exemplary in nature and is not intended to limit the scope, applicability, or configuration of the disclosure in any way. Unless defined otherwise, all technical and scientific terms used herein have the same meaning as those commonly understood by one of ordinary skill in the art to which this invention belongs. Although methods and materials similar or equivalent to those described herein may be used in the invention or testing, suitable methods and materials are described herein. The materials, methods and examples are illustrative only, and are not intended to be limiting. Those skilled in the art will recognize that many of the noted examples have a variety of suitable alternatives. The nomenclatures utilized in connection with, and the laboratory procedures and techniques of, analytical chemistry, synthetic organic chemistry, and medicinal and pharmaceutical chemistry described herein are those well-known and commonly used in the art. Standard techniques may be used for chemical syntheses, chemical analyses, pharmaceutical preparation, formulation, and delivery, and treatment of patients.

As used in the description herein and throughout the claims that follow, the meaning of "a," "an," and "the" includes plural reference unless the context clearly dictates otherwise.

"Attenuated," as used herein, means bacteria selected or altered to greatly diminish its capacity to cause disease, but still able to retain its ability to colonize the gut associated lymphoid tissue.

"Coding sequence" and "coding region," as used herein, are used interchangeably and refer to a polynucleotide that encodes a protein and, when placed under the control of appropriate regulatory sequences, expresses the encoded protein. The boundaries of a coding region are generally determined by a translation start codon at its 5' end and a translation stop codon at its 3' end.

"IL-2," as used herein, means the protein human interleukin-2.

"NK" or "NK cell," as used herein, means natural killer cell.

"Operably linked," as used herein, refers to a juxtaposition wherein the components so described are in a relationship permitting them to function in their intended manner. A regulator sequence is operably linked to a coding region when it is joined in such a way that expression of the coding region is achieved under conditions compatible with the regulatory sequence.

"Regulatory Sequence," as used herein, refers to a nucleotide sequence that regulates expression of a coding region to which it is operably linked. Non-limiting examples of regulatory sequences include promoters, transcription initiation sites, translation start sites, translation stop sites and terminators.

Attenuated *Salmonella typhimurium* has been developed as a vector to deliver therapeutic agents to tumors. The potential of *S. typhimurium* is largely due to its reported propensity to accumulate at greater than 1,000-fold higher concentration in tumors relative to healthy tissues. In addition, the genetic manipulability of *S. typhimurium* allows for the expression of foreign recombinant proteins, making these bacteria an effective delivery system for proteins that may be toxic when administered systemically.

Figure 3:
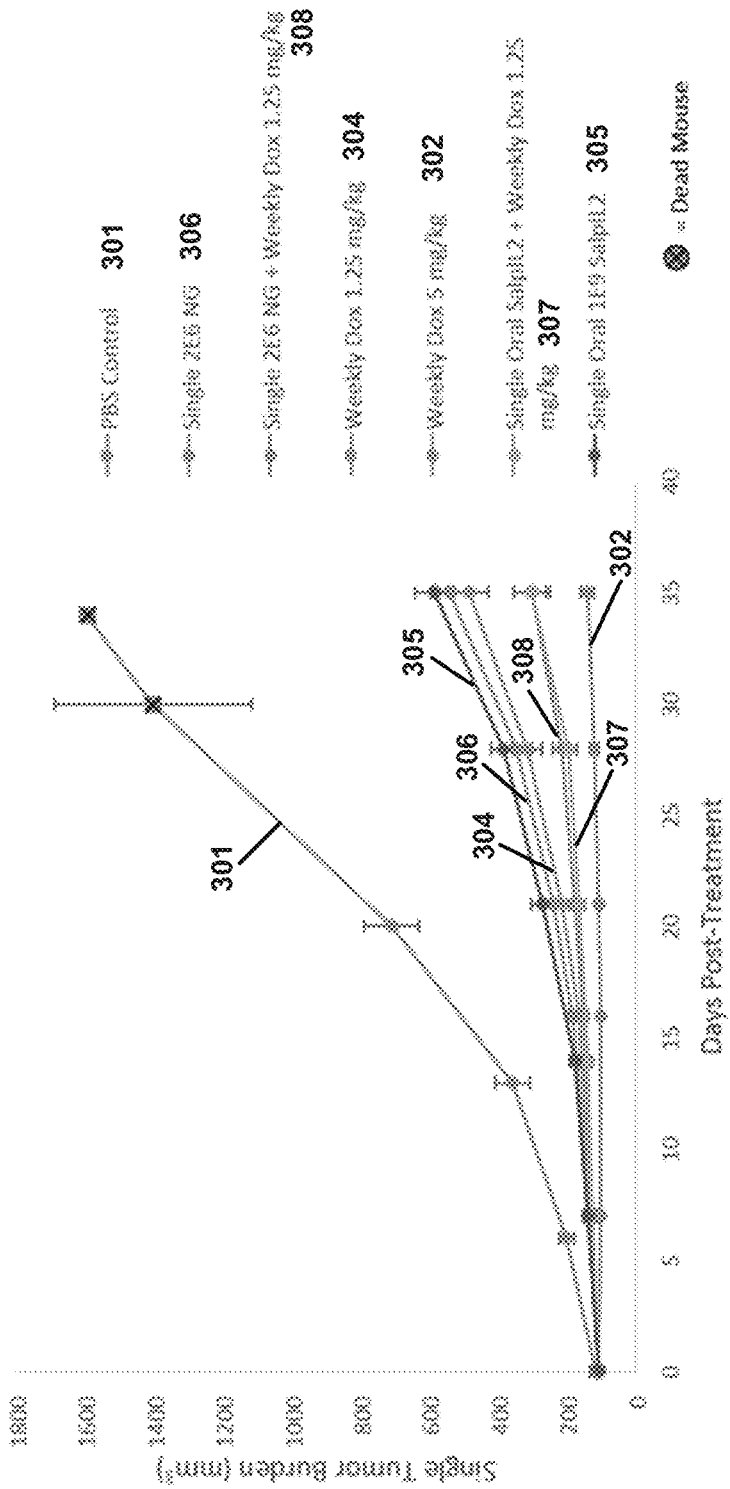
FIG. 3 is a line graph of single tumor burden versus days post-treatment in mice treated with combinations of attenuated *S. typhimurium* and doxorubicin compared to control groups.

Interleukin-2 (IL-2) is a protein naturally produced by the human body which promotes lymphocyte proliferation and enhances the cytolytic function of T cells and natural killer (NK) cells. It is thus able to stimulate the immune system to produce cancer-destroying white blood cells. IL-2 based immunotherapy in certain types of cancer has been studied for years with limited success. The amino acid sequence (SEQ ID NO: 3) of the normal human IL-2 protein encoded by SEQ ID NO: 4 (the DNA sequence encoding normal human IL-2) is shown in FIG. 3 of U.S. patent application Ser. No. 13/524,503 now U.S. Pat. No. 8,647,618, which is a continuation of U.S. patent application Ser. No. 12/425,927, filed Apr. 17, 2009 now U.S. Pat. No. 8,221,739, which is a continuation in part of and claims priority of U.S. patent application Ser. No. 10/834,587, filed Apr. 29, 2004 now abandoned, the contents of which applications are hereby incorporated by reference in their entirety.

While IL-2 is naturally produced by the human body, its maximum effectiveness requires a higher concentration and more specific delivery vector to the disease site. However, high doses of IL-2 are found to result in severe toxicity in many patients. A solution to this problem is using a live bacterial strain of *Salmonella typhimurium* which was attenuated to greatly diminish its capacity to cause disease. *S. typhimurium* is used due to its natural ability to colonize the gut associated lymphoid tissue (GALT), liver and spleen. Colonization of the liver by the attenuated *S. typhimurium* further initiates a generalized cellular response against the bacteria or can persist as a carrier state. The χ4550 strain of *S. typhimurium* used in the present disclosure contains a gene deletion constructed by transposon mutagenesis with Tn10 followed by selection for furanic acid resistance. This method of genetic alteration leads to deletional loss of Tn10 and adjacent DNA sequences to produce a deletion of aspartate semialdehyde dehydrogenase (asd). This mutation imposes a requirement for diaminopimelic acid. The lack of the asd enzyme in these bacteria leads to the inability to construct a stable cell wall causing lethal lysis of the *S.*

*typhimurium*. Thus, to insure stable expression of a desired protein, a plasmid (pYA292) was constructed which carries the asd gene.

FIG. 1A shows the pIL2 plasmid containing the coding sequence encoding the human interleukin-2 protein, used to construct SalpIL2, attenuated *S. typhimurium* with the IL-2 gene. In order to insure avirulence of the *S. typhimurium* strain, standard P22 phage transduction of the mouse virulent *S. typhimurium* SR-11 strain χ3306 was employed to construct the χ4550 strain that lacks the ability to synthesize adenylate cyclase and the cAMP receptor protein (CRP). Cyclic AMP and cAMP receptor protein are necessary for the transcription of many genes and operons concerned with the transport and breakdown of catabolites. Although cAMP is found in mammalian tissue and theoretically could be used by the bacteria to increase the potential for virulence, the lack of a cAMP receptor protein should abolish any benefit that could occur by the uptake of cAMP by these mutant bacteria.

A synthetic cDNA (SEQ ID NO: 5), coding for a truncated human IL-2 protein, optimized for expression in *Escherichia coli* was inserted into plasmid pYA292 using well known methods. The truncated cDNA (SEQ ID NO: 1) is a part of the synthetic IL-2 nucleotide sequence (SEQ ID NO: 5). This sequence is one nucleotide short of the sequence that was intended to code for a full-length mature human IL-2 protein. As used herein, "mature" means a protein lacking the beginning (N-terminal) 20 amino acid signal sequence that is cleaved off as the molecule is secreted from the a human cell. The mutation that occurred is a deletion of a "t" nucleotide between the "a" at position 272 and the "g" at position 273. This resulted in an in-frame taa stop codon at position 274 that truncated the resultant IL-2 protein. The resulting DNA nucleotide sequence is SEQ ID NO: 1 and the expressed protein is SEQ ID NO: 2.

Both the aspartate semialdehyde dehydrogenase (asd+) vector and the synthetic truncated human IL-2 cDNA were digested to completion with restriction enzymes EcoRI (Promega, Madison, Wis.) and HindIII (New England Biolabs, Beverly, Mass.). The about ~3.4 kb linearized vector fragment of pYA292 and the EcoRI-HindIII fragment of the IL-2 gene were isolated following agarose gel electrophoresis using the PrepaGene Kit (BioRad, Hercules, Calif.). The IL-2 gene fragment was ligated into the pYA292 vector using T4 DNA ligase (Promega, Madison, Wis.) with a 3:1 molar excess of insert and incubating for 4 hours at 16° C. The ligation mix was then electroporated into the χ4550 strain of attenuated *S. typhimurium*. *S. typhimurium*, Δcya-1 Δcrp-1 ΔasdA1 strain χ4550 was grown in Luria Broth (Sigma, St. Louis, Mo.) containing 50 mg/ml diaminopimelic acid (DAP).

Cultures were grown to an absorbance of 0.200 at $OD_{600}$ (approximately $10^8$ colony forming units (cfu)/ml broth) and the cells were prepared for electroporation. Plasmid vector pYA292 and the ligation mix were electroporated into χ4550 utilizing an electroporation device (BioRad) with 0.2 cm disposable cuvettes. Cells were pulsed at 2.5 kV and 25 μF with a pulse controller at 200 ohms. Cells were then subsequently plated on Luria agar without DAP and recombinant clones were identified using the Magic Mini-Prep DNA Purification System (Promega), and restriction enzyme digestion with EcoRI and HindIII and gel electrophoresis with 1.2 agarose. The restriction enzyme mapping revealed a plasmid corresponding to that expected for an insert of the IL-2 fragment in pYA292 and the plasmid was renamed pIL2. The new transformant was renamed χ4550 (pIL2), also referred to herein as "SalpIL2."

Transforming an asd deleted strain with the plasmid (pIL2) allows for the stable expression of IL-2. As discussed above, stability of this vector is maintained because the particular strain of *S. typhimurium* used here (χ4550) lacks the enzyme aspartate semialdehyde dehydrogenase (asd), which, conversely, the plasmid containing the IL-2 gene (pIL2) contains. Bacteria lacking asd cannot make diaminopimelic acid (DAP), an essential component of the bacterial cell wall and, thus, would not long survive. Thus, if the attenuated *S. typhimurium* were to attempt to revert to its wild-type strain and lose the plasmid, it would die a "DAP-less" death. Because the loss of the IL-2 containing plasmid would also result in the loss of the plasmid encoded asd, stable expression of the IL-2 gene is achieved.

FIG. 1B shows the pNG.1 plasmid without the coding sequence encoding the human interleukin-2 protein, which is used to construct SalpNG.1, attenuated *S. typhimurium* without the IL-2 gene. SalpNG.1 was constructed by transforming χ4550 with pNG.1, a plasmid containing cDNA coding for aspartate semialdehyde dehydrogenase to complement the χ4550 requirement for diaminopimelic acid. To construct plasmid pNG.1, plasmid pYA292 was cut with EcoRI and HindIII, the ends filled in, and the plasmid recircularized to eliminate the LacZ(alpha) coding sequence. Overnight cultures of SalpNG.1 were grown in lysogeny broth (LB) and flash frozen with liquid nitrogen in 15% glycerol in LB and stored at −80° C. Before treatment, bacteria were thawed at 37° C. and appropriately diluted in phosphate-buffered normal saline (PBS). The difference between SalpNG.1 and SalpIL2 is the presence of the truncated human IL-2 gene.

FIG. 2 is a flow diagram of method 200. Method 200 is a method of treating cancer with a combination of attenuated *S. typhimurium* and a chemotherapy agent according to various embodiments. Method 200 includes administering a first dose of attenuated *S. typhimurium* and a first dose of a chemotherapy agent (201), administering a second dose of attenuated *S. typhimurium* (202), administering a second dose of a chemotherapy agent (203), administering a third dose of attenuated *S. typhimurium* (204), and administering a third dose of a chemotherapy agent (205). Method 200 need not include all of the steps shown in FIG. 2. For example, in some embodiments, method 120 may exclude the steps of administering a second dose of attenuated *S. typhimurium* (202) and administering a third dose of attenuated *S. typhimurium* (204). Additionally, method 200 can include additional steps, such as administering a fourth dose of attenuated *S. typhimurium* and/or administering a fourth dose of the chemotherapy agent. The number of doses of attenuated *S. typhimurium* and the chemotherapy agent in method 200 can be varied depending on the organism and the type of cancer being treated.

In one embodiment, method 200 includes administering a first dose of attenuated *S. typhimurium* and a first dose of a chemotherapy agent (201) on a first day, administering a second dose of a chemotherapy agent (203) on a second day a week after the first day, and administering a third dose of a chemotherapy agent (205) on a third day a week after the second day. In this embodiment, a single dose of attenuated *S. typhimurium* is administered throughout the entire treatment period. In another embodiment, method 200 includes administering a first dose of attenuated *S. typhimurium* and a first dose of a chemotherapy agent (201) on a first day, administering a second dose of attenuated *S. typhimurium* (202) on a second day a week after the first day, administering a second dose of a chemotherapy agent (203) on the second day a week after the first day, and administering a third dose of a chemotherapy agent (205) on a third day a week after the second day. In this embodiment, two doses of attenuated *S. typhimurium* are administered throughout the entire treatment period.

In another embodiment, method 200 includes administering a first dose of attenuated *S. typhimurium* and a first dose of a chemotherapy agent (201) on a first day, administering a second dose of attenuated *S. typhimurium* (202) on a second day three weeks after the first day, administering a second dose of a chemotherapy agent (203) on the second day three weeks after the first day, administering a third dose of attenuated *S. typhimurium* (204) on a third day three weeks after the second day, and administering a third dose of a chemotherapy agent (205) on the third day three weeks after the second day. This embodiment further includes administering a fourth dose of attenuated *S. typhimurium* and a fourth dose of a chemotherapy agent on a fourth day three weeks after the third day, administering a fifth dose of attenuated *S. typhimurium* and a fifth dose of a chemotherapy agent on a fifth day three weeks after the fourth day, and administering a sixth dose of attenuated *S. typhimurium* and a sixth dose of a chemotherapy agent on a sixth day three weeks after the fifth day. In this embodiment, six doses of attenuated *S. typhimurium* are administered throughout the entire treatment period.

In some embodiments, administering the first dose of attenuated *S. typhimurium* (201) includes orally or intravenously administering the attenuated *S. typhimurium*. In one embodiment, administering a first dose of attenuated *S. typhimurium* (201) includes administering a oral dose of SalpIL2. In some embodiments, the dose is about $1 \times 10^9$ cfu. In another embodiment, administering a first dose of attenuated *S. typhimurium* (201) includes administering a intravenous (IV) dose of SalpNG.1. In some embodiments, the dose is about $2 \times 10^6$ cfu.

In some embodiments, administering a first dose of a chemotherapy agent (201) includes administering a IV dose of doxorubicin. In one embodiment, the dose of doxorubicin is 1.25 mg/kg. In another embodiment, the dose of doxorubicin is 2.5 mg/kg. In other embodiments, the chemotherapy agent can be carboplatin, cisplatin, cyclophosphamide, daunorubicin, oxaliplatin, 5-fluorouracil, gemcitabine, or any other appropriate chemotherapy agent.

Method 200 is advantageous, because the combination provides a synergistic effect that provides a greater reduction in tumor burden than the administration of the chemotherapy agent alone. As a result, a lower and less toxic dose of the chemotherapy agent can be used, which provides effective treatment while minimizing side effects caused by the toxicity of the chemotherapy agent.

EXAMPLES

BALB-neuT Tumor Treatment Model

The BALB-neuT model is a genetically engineered mouse model in which mammary tumor development is driven by expression of a constitutively activated rat homolog of human epidermal growth factor receptor 2. In this model, autochthonous tumors develop over several months and are palpable in the mammary pads of female mice around 16 weeks of age. The tumors closely resemble the aggressive Her2-driven cancer found in human patients.

BALB-neuT mice were maintained in specific pathogen free conditions and fed standard mouse chow (Harlan). Animals were cared for by the University of Minnesota's Research Animal Resources, and all animal use was approved by the University's Institutional Animal Care and Use Facility. Genotyping for the neu transgene was performed by Transnetyx on male and female pups. Breeding pairs consisted of heterozygous males and homozygous negative females. Female mice that were positive for the neu transgene were monitored for tumor development.

Methods

Female BALB-neu-T mice spontaneously developed palpable mammary fat pad tumors around 16 weeks of age (approximately 50-60 mm$^3$). At this time (day 0), the mice typically had 1-3 palpable tumors. For each experiment, individual tumors were measured by caliper, and their volume was calculated. Individual tumor volumes were calculated as spheroid (L×W$^2$×0.52) and combined to give a total tumor burden measurement for each mouse. Tumor burden data was gathered weekly from day 0 to day 35. Additionally, percent weight change data was gathered weekly for each mouse from day 0 to day 35. The percent weight change was calculated based on the baseline weight of each mouse.

Figure 2:
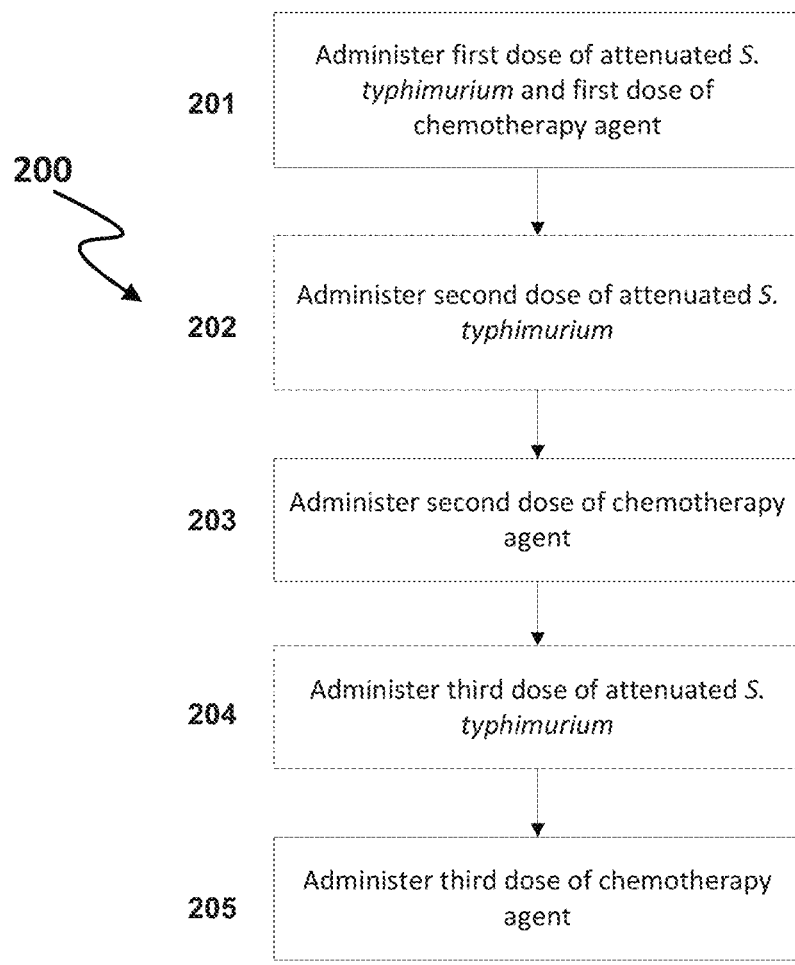
FIG. 2 is a flow diagram of a method of treating cancer with a combination of attenuated *S. typhimurium* and a chemotherapy agent according to various embodiments.

Various embodiments of method 200, described above with respect to FIG. 2, were used to treat tumors in the BALB-neuT model using combinations of attenuated *S. typhimurium* and the chemotherapy agent doxorubicin. A prescribed amount per cfu of the appropriate *S. typhimurium* strain (SalpIL2 or SalpNG.1) was administered via intravenous injection or gavage orally in 100 μL of PBS. The doxorubicin was administered intravenously via tail vein. Additionally, using the same methods of administration, a number of control groups received PBS alone, doxorubicin alone, SalpIL2 alone, or SalpNG.1 alone.

One control group (301) received PBS alone. For this control group, the tumors in the mice enlarged over time, and new tumors appeared on the remaining fat pads, usually until each mammary pad developed a tumor. When left untreated, average total tumor burden per mouse reached 5.66 cm$^3$ by day 35, at which point the mice were moribund and euthanized.

Three control groups received doxorubicin alone. The first control group (302) received the maximum tolerated dose (MTD) of intravenous (IV) 5 mg/kg doxorubicin on days 0, 7, and 14. The second control group (303) received IV 2.5 mg/kg (50% reduction in MTD) doxorubicin on days 0, 7 and 14. The third control group (304) received IV 1.25 mg/kg (75% reduction in MTD) doxorubicin on days 0, 7, and 14.

One control group (305) of mice received SalpIL2 alone. This control group received an oral dose of $1 \times 10^9$ cfu SalpIL2 on day 0 and did not receive any additional SalpIL2 or doxorubicin treatments. Another control group (306) received Salp NG.1 alone. This control group received an IV dose of $2 \times 10^6$ cfu SalpNG.1 on day 0 and did not receive any additional SalpNG.1 or doxorubicin treatments.

For combination therapy treatment with SalpIL2, one group of mice (307) received an oral dose of $1 \times 10^9$ cfu SalpIL2 as well as IV 1.25 mg/kg doxorubicin on day 0. Two additional doses of IV 1.25 mg/kg doxorubicin were administered on days 7 and 14. For combination therapy treatment with SalpNG.1, a first group of mice (308) received an IV dose of $2 \times 10^6$ cfu SalpNG.1 as well as IV 1.25 mg/kg doxorubicin on day 0. Two additional doses of IV 1.25 mg/kg doxorubicin were administered on days 7 and 14. A second group of mice (309) received an IV dose of $2 \times 10^6$ cfu SalpNG.1 as well as IV 2.5 mg/kg doxorubicin on day 0. Two additional doses of IV 2.5 mg/kg doxorubicin were administered on days 7 and 14.

Results

FIGS. 3-6 show the results of tumor treatment in the BALB-neuT model using combinations of attenuated *S. typhimurium* and the chemotherapy agent doxorubicin as compared to a number of control groups that received PBS alone, doxorubicin alone, SalpIL2 alone, or SalpNG.1 alone. The data shown includes day 0, on which the first treatment was administered, day 14 on which a second treatment was administered, and day 21, on which a third treatment was administered. Subsequent data points were taken post-treatment on days 28 and 35.

FIG. 3 is a line graph of single tumor burden versus days post-treatment in mice treated with combinations of attenuated *S. typhimurium* and doxorubicin compared to control groups. In the PBS control group (301), the mice did not survive or were moribund and euthanized by day 30 or 35. In the group that received the MTD of 5 mg/kg of doxorubicin (302), the tumor burden was the lowest and remained around 100 mm$^3$ at day 35. In the group that received 25% of the MTD of doxorubicin, i.e. 1.25 mg/kg of doxorubicin (304), the tumor burden was almost double that of the group that received the MTD of doxorubicin (302) by day 21, and almost 5 times as high by day 35. The groups that received a single oral dose of SalpIL2 (305) and a single IV dose of SalpNG.1 (306) showed a similar trend to that of the group that received 1.25 mg/kg of doxorubicin (304).

The group that received a combination of oral SalpIL2 and 1.25 mg/kg doxorubicin (307) and the group that received a combination of IV SalpNG.1 and 1.25 mg/kg doxorubicin (308) surprisingly showed a synergistic effect in tumor treatment. A statistically significant reduction in tumor burden is shown. The tumor burden by day 21 was less than double that of the group that received the MTD of doxorubicin (302), and was only slightly more than double by day 35. Unexpectedly, there was no difference in the combination treatment with the oral SalpIL2 and the combination treatment with the IV SalpNG.1. Thus, the combination treatments of 1.25 mg/kg of doxorubicin with either SalpIL2 or SalpNG.1 are nearly as effective as treatment with the MTD of doxorubicin alone and significantly more effective than treatment with 1.25 mg/kg of doxorubicin alone. The dose of doxorubicin in the combination treatments is only 25% of the MTD, which significantly reduces the toxic effects of the doxorubicin (explained in greater detail below with respect to FIG. 6).

Figure 4:
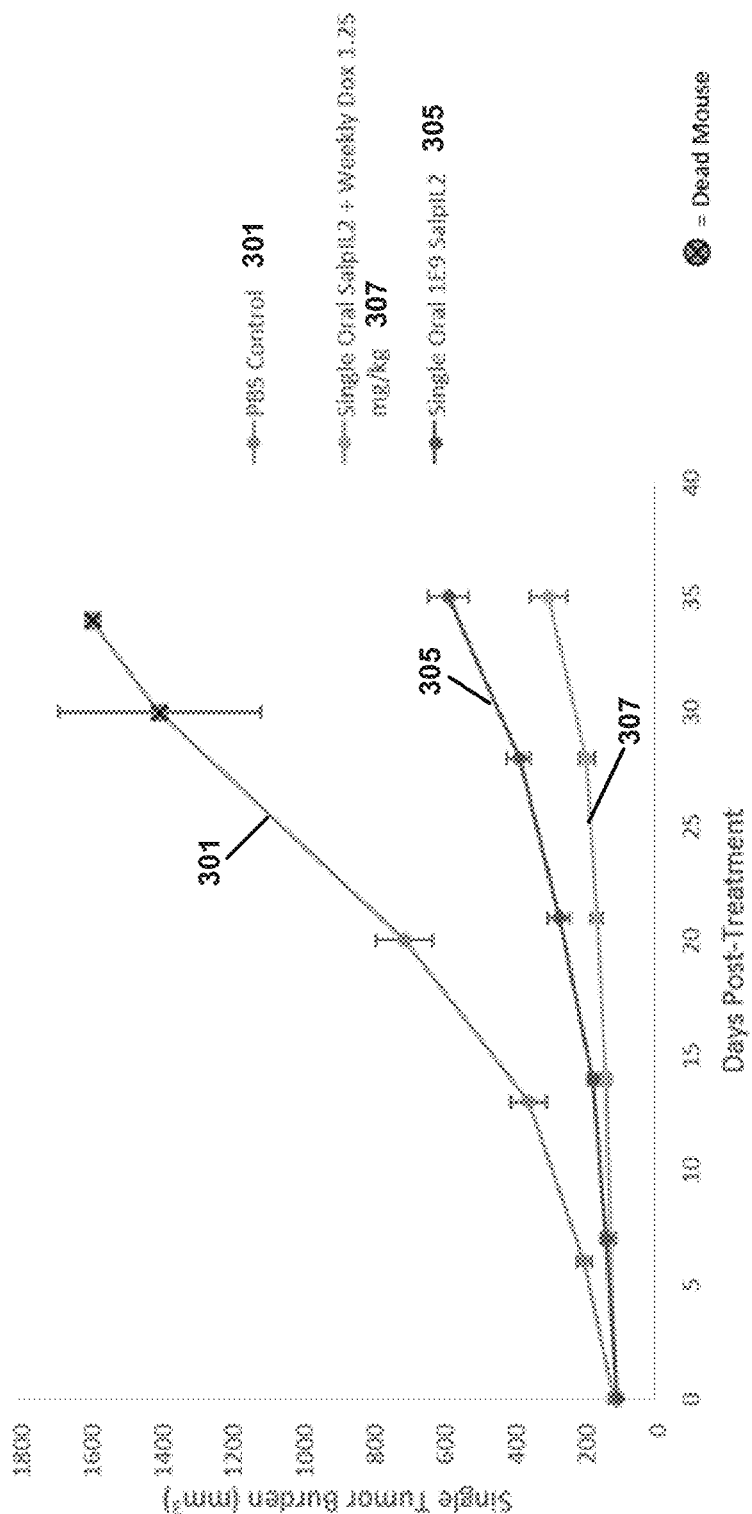
FIG. 4 is a line graph of single tumor burden versus days post-treatment in mice treated with a combination of SalpIL2 and doxorubicin compared to control groups.

FIG. 4 is a line graph of single tumor burden versus days post-treatment in mice treated with a combination of SalpIL2 and doxorubicin compared to control groups. As explained above with respect to FIG. 3, in the PBS control group (301), the mice did not survive or were moribund and euthanized by day 30 or 35. A statistically significant reduction in tumor burden is shown in the group that received a combination of a single oral dose of SalpIL2 and 1.25 mg/kg doxorubicin (307) as compared to the control group that received only a single oral dose of SalpIL2. The tumor burden of the control group that received a single oral dose of SalpIL2 (305) was double that of the group that received the combination of SalpIL2 and 1.25 mg/kg doxorubicin (307) by day 35. This further demonstrates the synergistic effect of the combination treatment of oral SalpIL2 and 1.25 mg/kg doxorubicin.

Figure 5:
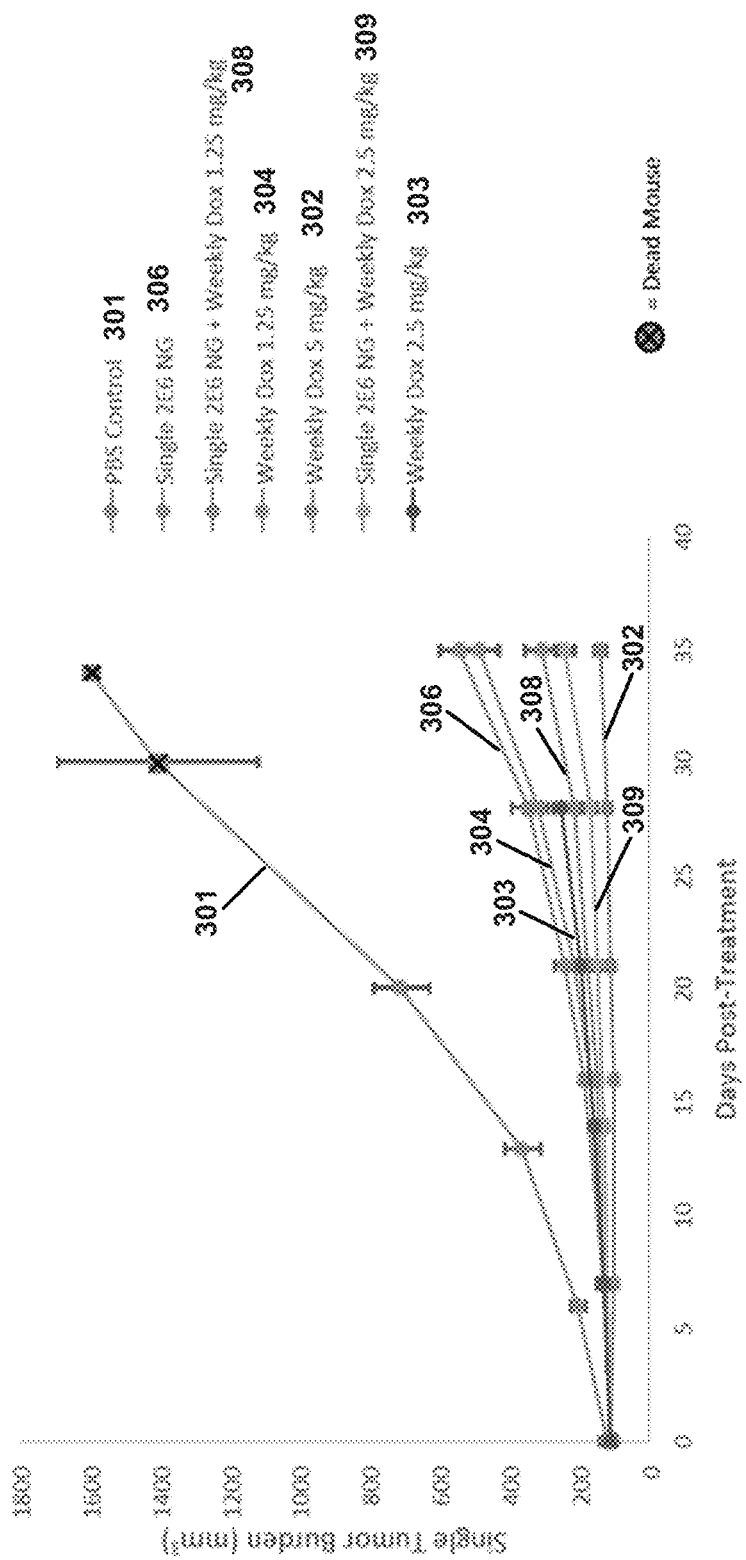
FIG. 5 is a line graph of single tumor burden versus days post-treatment in mice treated with combinations of SalpNG.1 and doxorubicin compared to control groups.

FIG. 5 is a line graph of single tumor burden versus days post-treatment in mice treated with combinations of SalpNG.1 and doxorubicin compared to control groups. As explained above with respect to FIG. 3, in the PBS control group (301), the mice did not survive or were moribund and euthanized by day 30 or 35. In the control group that received the MTD of 5 mg/kg of doxorubicin (302), the tumor burden was the lowest and remained around 100 mm$^3$ at day 35. In the control group that received 25% of the MTD of doxorubicin, i.e. 1.25 mg/kg of doxorubicin (304), the tumor burden was almost double that of the group that received the MTD of doxorubicin by day 21, and almost 5 times as high by day 35. In the control group that received 50% of the MTD of doxorubicin, i.e. 2.5 mg/kg of doxorubicin (303), as expected, the tumor burden was in between that of the control group that received the MTD of doxorubicin (302) and the group that received 1.25 mg/kg of doxorubicin (304).

The group that received a combination of IV SalpNG.1 and 1.25 mg/kg doxorubicin (308) showed a synergistic effect in tumor treatment. A statistically significant reduction in tumor burden is shown. The tumor burden by day 21 was less than double that of the group that received the MTD of doxorubicin (302), and was only slightly more than double by day 35. The group that received a combination of IV SalpNG.1 and 2.5 mg/kg doxorubicin (309) also showed a synergistic effect in tumor treatment. A statistically significant reduction in tumor burden is also shown for this group. The tumor burden by day 21 was even less than the tumor burden in the group that received a combination of SalpNG.1 and 1.25 mg/kg, and by day 35 was barely double the tumor burden of the group that received the MTD of doxorubicin (302).

Thus, the combination treatments of SalpNG.1 with 1.25 mg/kg of doxorubicin or 2.5 mg/kg doxorubicin are nearly as effective as treatment with the MTD of doxorubicin alone and significantly more effective than treatment with 1.25 mg/kg of doxorubicin alone or 2.5 mg/kg of doxorubicin alone. This further demonstrates the synergistic effect of the combination treatment of IV SalpNG.1 and 1.25 mg/kg doxorubicin, as well as demonstrates the synergistic effect of the combination treatment of IV SalpNG.1 and 2.5 mg/kg of doxorubicin.

Figure 6:
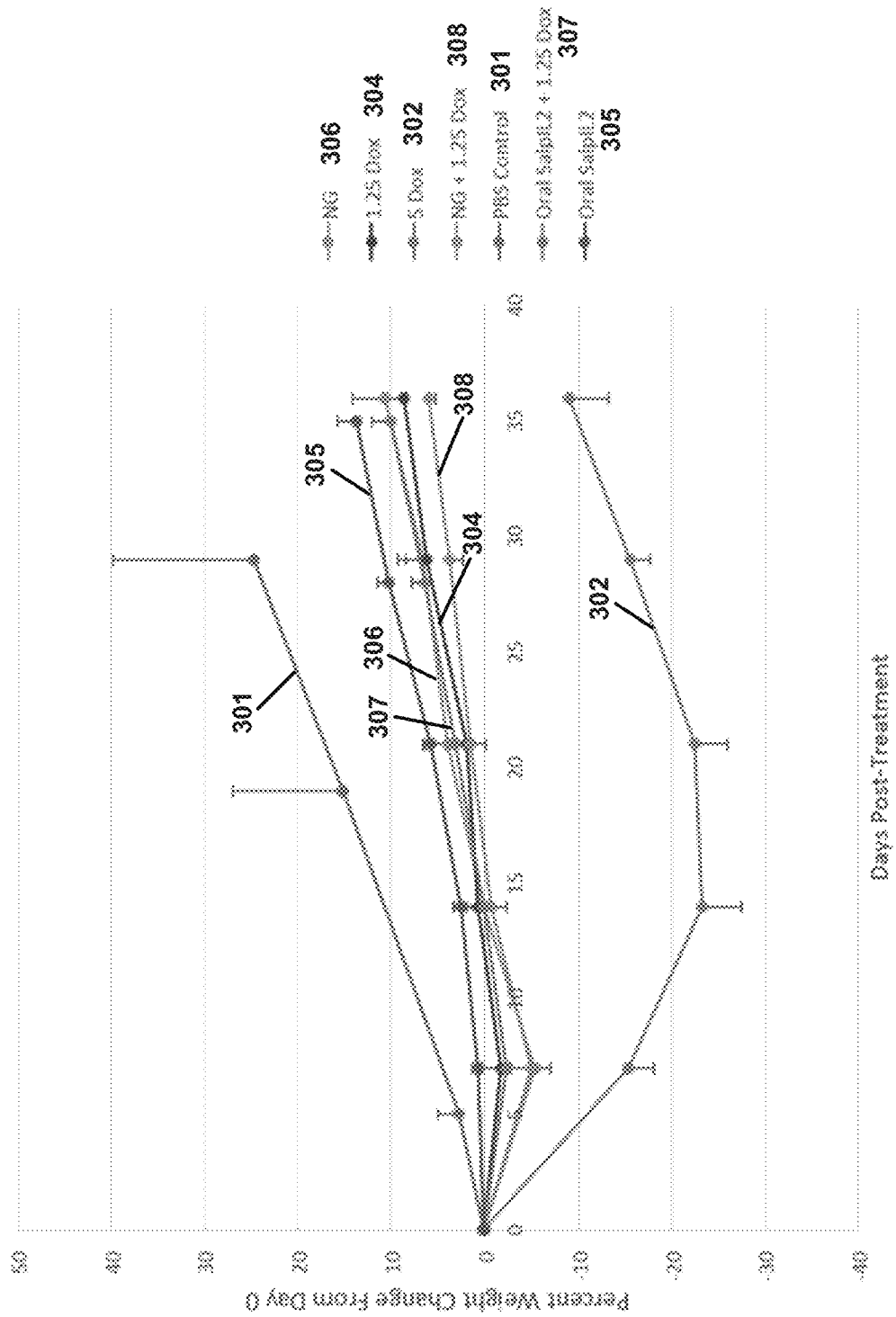
FIG. 6 is a line graph of percent weight change versus days post-treatment in mice treated with combinations of attenuated *S. typhimurium* and doxorubicin compared to control groups.

FIG. 6 is a line graph of percent weight change versus days post-treatment in mice treated with combinations of attenuated *S. typhimurium* and doxorubicin compared to control groups. Weight change in mice is an accurate measure of the degree of toxicity of a chemotherapy agent. Significant weight loss translates to significant toxicity. While the control group that received PBS (301) saw a greater than 25% increase in weight by day 30, the mice in that group died or were moribund and euthanized due to tumor growth. The control group that received the MTD dose of 5 mg/kg of doxorubicin (302) showed a significant reduction in weight, with a loss of greater than 20% by day 14 and almost 10% by day 35. This indicates significant toxicity of the MTD dose of doxorubicin. The group that received 25% of the MTD dose of doxorubicin, i.e. 1.25 mg/kg of doxorubicin (304), did not show any weight loss by day 14 and showed less than a 10% weight gain by day 35, and thus was deemed non-toxic. The group that received a single oral dose of SalpIL2 (305) showed a slight weight gain by day 14 and almost a 15% weight gain by day 35. The control group that received a single IV dose of SalpNG.1 (306) showed no weight loss by day 14 and about a 10% weight gain by day 35.

The group that received a combination treatment of oral SalpIL2 and 1.25 mg/kg of doxorubicin (307) did not show any weight loss by day 14 and showed about a 10% weight gain by day 35. The group that received a combination treatment of IV SalpNG.1 and 1.25 mg/kg of doxorubicin (308) showed a slight weight loss by day 14 and greater than a 5% weight gain by day 35. This data further supports the synergistic effect of combination treatments of doxorubicin with attenuated *S. typhimurium* with minimal or no toxicity.

As explained with respect to FIGS. 3-5, treatments with 1.25 mg/kg of doxorubicin in combination with oral SalpIL2 or IV SalpNG.1 are nearly as effective as treatment with the MTD of doxorubicin alone and significantly more effective than treatment with 1.25 mg/kg of doxorubicin alone. The dose of doxorubicin in the combination treatments is only 25% of the MTD, which significantly reduces the toxic effects of the doxorubicin, as evidenced by the statistically significant reduction in weight loss shown in FIG. 6. Therefore, the synergistic effect of combination treatments of a significantly less toxic dose of doxorubicin combined with an appropriate attenuated *S. typhimurium* strain provides an effective tumor treatment while minimizing the negative side effects, such as weight loss, of chemotherapy agents.

The invention claimed is:

1. An anti-tumor agent for treating cancer, comprising: a combination of a dose of a chemotherapy agent and a dose of attenuated *Salmonella typhimurium* containing a plasmid carrying a coding sequence encoding a human interleukin-2, wherein the human interleukin-2 consists of the amino acid sequence shown in SEQ ID NO: 2; wherein the chemotherapy agent comprises at least one agent selected from the group consisting of doxorubicin, carboplatin, cyclophosphamide, daunorubicin, oxaliplatin, 5-fluorouracil, and gemcitabine; wherein the dose of the chemotherapy agent is less than a maximum tolerated dose of the chemotherapy agent; wherein the combination provides a synergistic reduction in tumor burden when compared to the reduction in tumor burden provided by administration of an equivalent dose of the chemotherapy agent without the attenuated *Salmonella typhimurium* containing the plasmid carrying the coding sequence encoding the human interleukin-2; and wherein the toxicity of the combination is lower than the toxicity of the maximum tolerated dose of the chemotherapy agent.

2. The anti-tumor agent of claim 1, wherein the dose of the chemotherapy agent is 25% of the maximum tolerated dose of the chemotherapy agent.

3. The anti-tumor agent of claim 1, wherein the dose of attenuated *Salmonella typhimurium* containing the plasmid carrying the coding sequence encoding the human interleukin-2 is $1 \times 10^9$ colony forming units.

4. The anti-tumor agent of claim 1, wherein the attenuated *Salmonella typhimurium* containing the plasmid carrying the coding sequence encoding the human interleukin-2 is administered orally.

5. The anti-tumor agent of claim 1, wherein a first dose of the chemotherapy agent and the dose of the attenuated *Salmonella typhimurium* containing the plasmid carrying the coding sequence encoding the human interleukin-2 are administered on a first day.

6. The anti-tumor agent of claim 5, wherein a second dose of the chemotherapy agent is administered on a second day a week after the first day.

7. The anti-tumor agent of claim 6, wherein a third dose of the chemotherapy agent is administered on a third day a week after the second day.

8. The anti-tumor of claim 5, wherein a plurality of doses of the chemotherapy agent and a plurality of doses of the attenuated *Salmonella typhimurium* are administered on a plurality of days after the first day.

9. A method of treating cancer, the method comprising: administering a combination of a dose of a chemotherapy agent and a dose of attenuated *Salmonella typhimurium* containing a plasmid carrying a coding sequence encoding a human interleukin-2, wherein the human interleukin-2 consists of the amino acid sequence shown in SEQ ID NO: 2; wherein the chemotherapy agent comprises at least one agent selected from the group consisting of doxorubicin, carboplatin, cyclophosphamide, daunorubicin, oxaliplatin, 5-fluorouracil, and gemcitabine; wherein the dose of the chemotherapy agent is less than a maximum tolerated dose of the chemotherapy agent; wherein the combination provides a synergistic reduction in tumor burden when compared to the reduction in tumor burden provided by administration of an equivalent dose of the chemotherapy agent without the attenuated *Salmonella typhimurium* containing the plasmid carrying the coding sequence encoding the human interleukin-2; and wherein the toxicity of the combination is lower than the toxicity of the maximum tolerated dose of the chemotherapy agent.

10. The method of claim 9, wherein the dose of the chemotherapy agent is 25% of the maximum tolerated dose of the chemotherapy agent.

11. The method of claim 9, wherein the dose of attenuated *Salmonella typhimurium* containing the plasmid carrying the coding sequence encoding the human interleukin-2 is $1\times10^9$ colony forming units.

12. The method of claim 9, wherein the attenuated *Salmonella typhimurium* containing the plasmid carrying the coding sequence encoding the human interleukin-2 is administered orally.

13. The method of claim 9, wherein a first dose of the chemotherapy agent and the dose of the attenuated *Salmonella typhimurium* containing the plasmid carrying the coding sequence encoding the human interleukin-2 are administered on a first day.

14. The method of claim 13, wherein a second dose of the chemotherapy agent is administered on a second day a week after the first day.

15. The method of claim 14, wherein a third dose of the chemotherapy agent is administered on a third day a week after the second day.

16. The method of claim 13, wherein a plurality of doses of the chemotherapy agent and a plurality of doses of the attenuated *Salmonella typhimurium* are administered on a plurality of days after the first day.

\* \* \* \* \*

SEQUENCE LISTING

```
Sequence total quantity: 2
SEQ ID NO: 1            moltype = DNA  length = 276
FEATURE                 Location/Qualifiers
source                  1..276
                        mol_type = genomic DNA
                        organism = Homo sapiens
SEQUENCE: 1
atggctccta ctagctcgag cactaagaaa actcaactgc aattggagca tctgctgctg   60
gatctgcaga tgattctgaa tggcatcaat aactacaaga accctaagct gactcgcatg  120
ctgactttca aattctacat gccgaaaaag gctaccgagc tcaaacatct ccagtgcctg  180
gaagaggaac tgaagccgct ggaggaagta cttaacctgg cacagtctaa gaacttccac  240
ctgcgtccgc gtgacctgat ctccaacatc aagtaa                            276

SEQ ID NO: 2            moltype = AA  length = 91
FEATURE                 Location/Qualifiers
source                  1..91
                        mol_type = protein
                        organism = Homo sapiens
SEQUENCE: 2
MAPTSSSTKK TQLQLEHLLL DLQMILNGIN NYKNPKLTRM LTFKFYMPKK ATELKHLQCL   60
EEELKPLEEV LNLAQSKNFH LRPRDLISNI K                                  91
```